United States Patent
Attila

(10) Patent No.: US 7,963,285 B2
(45) Date of Patent: Jun. 21, 2011

(54) ADHESIVE CONDOM AND DEPLOYMENT

(76) Inventor: Mady Attila, Kihei, HI (US)

( * ) Notice: Subject to any disclaimer, the term of this patent is extended or adjusted under 35 U.S.C. 154(b) by 592 days.

(21) Appl. No.: 11/868,094

(22) Filed: Oct. 5, 2007

(65) Prior Publication Data

US 2009/0090368 A1    Apr. 9, 2009

(51) Int. Cl.
- A61F 6/02 (2006.01)
- A61F 6/04 (2006.01)
- A61F 5/00 (2006.01)
- A41D 19/00 (2006.01)
- B05D 3/00 (2006.01)

(52) U.S. Cl. ........ 128/844; 128/842; 128/917; 128/918; 427/2.3; 600/38; 602/902

(58) Field of Classification Search ............... 128/844, 128/918, 842; 427/2.3; 604/352, 351; 600/38; 602/902

See application file for complete search history.

(56) References Cited

U.S. PATENT DOCUMENTS

| | | | |
|---|---|---|---|
| 1,225,341 A | 5/1917 | Lederer | |
| 3,495,589 A | 2/1970 | Clement | |
| 3,536,066 A | 10/1970 | Ludwig | |
| 4,004,591 A | 1/1977 | Freimark | |
| 4,378,008 A | 3/1983 | Osbon, Sr. | |
| 4,576,156 A | 3/1986 | Dyck et al. | |
| 4,664,104 A | 5/1987 | Jaicks | |
| 4,735,621 A | 4/1988 | Hessel | |
| 4,808,174 A | 2/1989 | Sorkin | |
| 4,817,593 A | 4/1989 | Taller et al. | |
| 4,829,991 A * | 5/1989 | Boeck | 600/38 |
| 4,855,169 A | 8/1989 | McGlothlin et al. | |
| 4,869,723 A | 9/1989 | Harmon | |
| 4,898,184 A | 2/1990 | Skurkovich et al. | |
| 4,920,983 A * | 5/1990 | Jimenez et al. | 128/844 |
| 4,934,382 A * | 6/1990 | Barone, Jr. | 128/844 |
| 4,993,431 A | 2/1991 | Reddy | |
| 4,993,433 A | 2/1991 | Reddy | |
| 5,109,871 A | 5/1992 | Thornton | |
| 5,112,900 A | 5/1992 | Buddenhagen et al. | |
| 5,121,755 A * | 6/1992 | Hegedusch | 128/844 |
| 5,137,032 A | 8/1992 | Harmon | |
| 5,331,974 A | 7/1994 | Sook | |
| 5,333,621 A | 8/1994 | Denzer | |
| 5,370,131 A | 12/1994 | Hess | |
| 5,413,117 A | 5/1995 | Wills | |
| 5,421,350 A | 6/1995 | Friedman | |
| 5,437,286 A | 8/1995 | Stratton | |
| 5,458,114 A | 10/1995 | Herr | |
| 5,469,863 A | 11/1995 | Shah | |
| 5,471,998 A | 12/1995 | Kuyumciyan | |
| 5,513,654 A | 5/1996 | Delson | |
| 5,549,120 A | 8/1996 | Persson et al. | |
| 5,551,612 A | 9/1996 | Hochfeld | |
| 5,601,092 A | 2/1997 | Miller et al. | |

(Continued)

FOREIGN PATENT DOCUMENTS

KR    WO0226174    4/2002

(Continued)

*Primary Examiner* — Patricia M Bianco
*Assistant Examiner* — Brandon Jackson

(57) ABSTRACT

Means of easy manufacture and deployment of condoms are provided. A practical and inexpensive adhesive condom is achieved to augment user satisfaction, provide increased barrier protection and contraceptive efficacy. Compression to the penis is reduced, thereby facilitating the ease of attaining and maintaining erection, improving barrier protection and preventing the transmission of sexually transmitted diseases, as well as increasing utilization rates by enhancing sensation.

17 Claims, 6 Drawing Sheets

U.S. PATENT DOCUMENTS

| | | |
|---|---|---|
| 5,603,335 A | 2/1997 | McClenahan |
| 5,623,946 A | 4/1997 | Hessel |
| 5,651,374 A | 7/1997 | Wester |
| 5,662,214 A | 9/1997 | Wood |
| 5,715,839 A | 2/1998 | Strauss et al. |
| 5,803,085 A | 9/1998 | Asinovsky |
| 5,806,524 A | 9/1998 | Hernandez |
| 6,148,819 A * | 11/2000 | Winkler ................. 128/842 |
| 6,425,397 B1 | 7/2002 | Liehs |
| 6,536,438 B1 | 3/2003 | Kakonyi |
| 6,776,755 B1 * | 8/2004 | Raskin ................... 600/39 |
| 6,840,244 B2 | 1/2005 | Kemp |
| 7,086,403 B2 * | 8/2006 | Harrison et al. .......... 128/844 |
| 7,592,021 B2 * | 9/2009 | Shankar et al. ........... 424/484 |
| 2006/0137692 A1 | 6/2006 | Samuelsson |

FOREIGN PATENT DOCUMENTS

| | | |
|---|---|---|
| WO | WO 03/037232 A1 * | 5/2003 |

\* cited by examiner

Figure 3
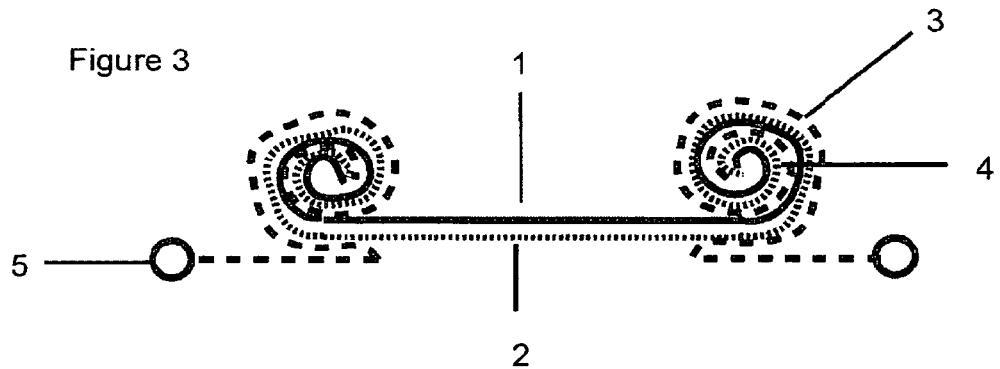
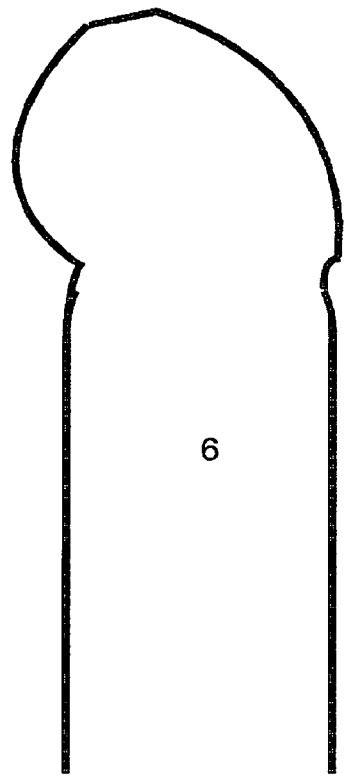

ADHESIVE CONDOM AND DEPLOYMENT

TECHNICAL FIELD

Condom, contraception, disease prevention, health and personal hygiene and sexual devices.

BACKGROUND OF THE INVENTION

Sexually transmitted diseases (STDs) remain an unresolved scourge of humanity.

Some such diseases, such as the plague and Bartonellosis, are transmitted through vectors and are not amenable to barrier type protection. However, the best protection for all other known STDs remains the condom.

Condoms are currently constructed of primarily elastic artificial membranes applied to the penis. Most are made of latex, shipped rolled into a ring form and deployed by unrolling onto the penis. Considerable ingenuity is sometimes utilized in deploying these condoms in intimate settings. For this reason users have been very reluctant to adopt modifications. Many adhesive type modifications have been proposed, but they have failed to gain any acceptance. Most due to the fact that they are useless, rendering condoms into no more than a disposable foreign body to interfere with intercourse. The remaining ones have failed due to inconvenience of use.

Most modifications proposed by prior art are not only inconvenient, but impractical and in many instances dangerous. In any case, most proposed changes compromise condoms' function as a barrier type of protectant and contraceptive.

Nevertheless, improvement in condom technology is imperative. Condoms are a necessary evil at best and outright harmful in some situations. They are much less effective than the 93% contraceptive efficacy advertised. They are cynically promoted as effective against STDs, when in fact they are only reliably effective (if used perfectly) against one entity: syphilis.

Condoms work against syphilis because the causative organism, a spirochete known as Treponema Pallidum, is very fragile. In fact, T. Pallidum dies immediately once the bodily fluids carrying it dry out. Treponema are also relatively large in size. For this reason, any crude barrier that simply separates the non-infected party from the partner will serve as a protectant.

This is not the case with gonorrhea and Chlamydia. This is even less the case with viruses. In fact, condoms are completely useless for the prevention of the transmission of the herpes virus. Hepatitis B, hepatitis C and even HIV are only partially prevented with condoms.

All of the above is only assuming appropriate use. Breakage during use, combination with solvents and a wide range of creative sexual endeavors that sometimes strain belief invalidate any possible protective use of condoms.

Finally, none of the above have any relevance in the setting of omission of condom use. Condoms are uniformly detested. Women don't like it because they reduce the male's sexual ardor and males ostensibly dislike them because they "reduce sensation". This is probably a fictitious, as condoms' greatest nuisance lies in the compression to which they subject the penis. Sufficient compression to maintain the condom on the penis invariably interferes with erection, both lessening its intensity and duration. Condoms therefore have very low rates of usage.

Condoms nevertheless are the only reasonable alternative to mass prevention of STDs and birth control. They are reasonably effective if used adequately for a limited set of clinical scenarios, they do prevent conception and are so inexpensive that third world economies can afford them for their public health needs. Significant improvement in the state of the art without significant increase in cost is likely to result in a momentous impact in the prevalence of STDs.

Lexicon

The condom of claim 1 is that cylindrical pliable membrane designed to be retained on the male sexual organ (penis, phallus) during sexual intercourse.

The apposed membrane applied to the inner surface of the condom of Claim 1 is a membrane that does not adhere to (or adheres only very weakly) to the adhesive on the inner surface of the condom, is intended only for the packaging and deployment of the condom and is discarded after deployment of said condom.

For the purposes of this patent, the PROXIMAL end of the condom of Claim 1 is defined as that end of the condom that would transmit the opening permitting application of the condom. This convention is in accordance with anatomical convention.

The DISTAL end of the condom shall therefore be defined as the reservoir tip, the valvular apparatus described in the separate but concurrent application, or whatever part of the condom that is applicable to the glans penis.

In contrast, the DISTAL end of the inner protective membrane approximated to the inner adhesive layer of the condom specified in Claim 1 shall be defined as the end that would approximate closest to the area next to the DISTAL aspect of the condom itself (specifically, to the reservoir tip of the condom). Note, this correspondence is not exact, as the inner adhesive of the condom of Claim 1 corresponding to the distal aspect of the glans penis is to remain exposed.

Accordingly, the PROXIMAL end of the inner protective layer would correspond to the PROXIMAL end of the condom of Claim 1 and is provided rolled up as described in the Claims.

(****Note that the above convention is based on the geometry PRIOR to deployment. The act of deployment will reverse the orientation of the inner membrane in such as manner as to deliver the DISTAL end past the PROXIMAL end, to base of the penis. Separation of the two membranes will thus initiate at their DISTAL ends and proceed towards the proximal end. The PROXIMAL ends of the two membranes will thus remain in contact until the very last moments prior to complete separation.)

STD—Sexually Transmitted Disease, a disease transmissible through the act of sexual intercourse.

The term target shall refer to the penis.

The term glans shall refer to glans penis, the terminal segment of the penis.

BACKGROUND ART

Extensive prior art is provided to illustrate the state of condom technology and the practical range of executable devices (i.e.: materials technology, geometries, efficacy, etc.). While there are a myriad of prior patents prescribing some manner of adhesion, there none in either US or Worldwide patent literature referring to full length condoms with adhesive use along the entire length of the condom. Presumably this is because of difficulty of deployment.

Two prior US patents (U.S. Pat. Nos. 5,421,350 & 5,458,114) and one foreign patent (SE521418, USPTO PUB #US2006137692) prescribe a condom affixed to the end of the penis. Partial length condoms, particularly those suggested to cover only the glans penis, are useless (and hazardous) unless the recipient is a midget with an orifice of microscopic depth acted upon by a giant with a penis of unnatural dimensions. Unless each new condom is surgically affixed to the skin of the penis and/or unless a permanent glue such as methyl methylacrylate (Crazy Glue™) is used to somehow weld the leading edge of the condom to the shaft, the free edge of the condom will roll off the penis, thus rendering it useless.

One prior patent (U.S. Pat. No. 6,536,438) proposes using an adhesive only proximally. This would again defeat the purpose of attempting to improve a condom, namely better adherence. The adhesive would have to be very strong and (since there would be high stress at the glued/non-glued interface), the condom would be MORE, not less likely to tear.

Several other patents are cited proposing various means of providing improved adherence without the use of adhesives (U.S. Pat. Nos. 5,513,654 & 5,715,839, WO0226174). Aside from the obvious flaw of trying to achieve something easily achieved with adhesives through ridiculously convoluted means, none of these embodiments are practical. The target is a tumescent organ that is subject to detumescence. Nothing but an adhesive would maintain close contact under such circumstances. Further, several of the cited means propose increased compression as a means of gaining better traction, increasing the probability of detumescence and thus reducing security rather than enhancing it.

One patent (U.S. Pat. No. 5,603,335) proposes an intraurethral condom. This is not only silly, but also dangerous. Prevention of conception is a distant secondary function of condoms, as condoms are notoriously unreliable in this regard. Inserting a condom into the urethra or a repeat basis is further guaranteed to result in trauma, thus causing emission of blood along with semen and increasing the odds of STD transmission.

The female anatomy hasn't escaped unscathed from attempts to protect it, either. U.S. Pat. No. 5,623,946 proposed an improved receptive geometry integrating a ring at the introitus. Aside from the lack of popularity of female condoms (nobody outside the homosexual community uses them), this arrangement increases the chances of a tear at the ring/condom interface.

Several patents are cited to illustrate the range of means to enhance the ease of condom deployment (U.S. Pat. Nos. 5,471,998, 5,549,120, 5,651,374 & 5,662,214). Without fail these proposals are convoluted, expensive and impractical. Indeed, no practical means of deployment has ever been proposed for an adhesive condom, much less one that not only rivals but actually surpasses current devices in terms of ease of use.

Overall, no prior art has recognized and specifically pointed out that a membrane backed by a substance with greater structural integrity acquires some of the structural integrity of that backing substance. A fully adherent condom is therefore stronger and more secure than a non-adhesive condom of the same material and of equal thickness. A firm adhesive thus permits constructing condoms of a much thinner gauge than non-adhesive embodiments.

The second unrecognized factor is that a membrane that is adherent to the skin will enhance sensation (if the membrane is "tuned" correctly). This is in contrast to a membrane that is allowed to slide over skin. Yet there are a number of prior patents that specifically recommend enhancing the condom's ability to move freely over skin. This not only compromises the condom's sensitivity by acting as an attenuator of microvibrations produced by friction, but also compromises the condom's safety and efficacy both as barrier-type contraception, and also a prophylactic of Sexually Transmitted Diseases.

BRIEF SUMMARY OF THE INVENTION

Means of easy manufacture and deployment of condoms are provided. A supportive membrane is used to assist in rolling the condom and protecting its inner surface, as well as a practical and inexpensive adhesive condom is achieved to augment user satisfaction, provide increased barrier protection and contraceptive efficacy. Compression to the penis is reduced, thereby facilitating the ease of attaining and maintaining erection, improving barrier protection and preventing the transmission of sexually transmitted diseases, as well as increasing utilization rates by enhancing sensation.

DESCRIPTION OF THE DRAWINGS

Sheet 1 (FIGS. 1 and 1A, longitudinal view in cross section) show a non-deployed device before and after rolling it into its final packed form, respectively.

Figure 1:
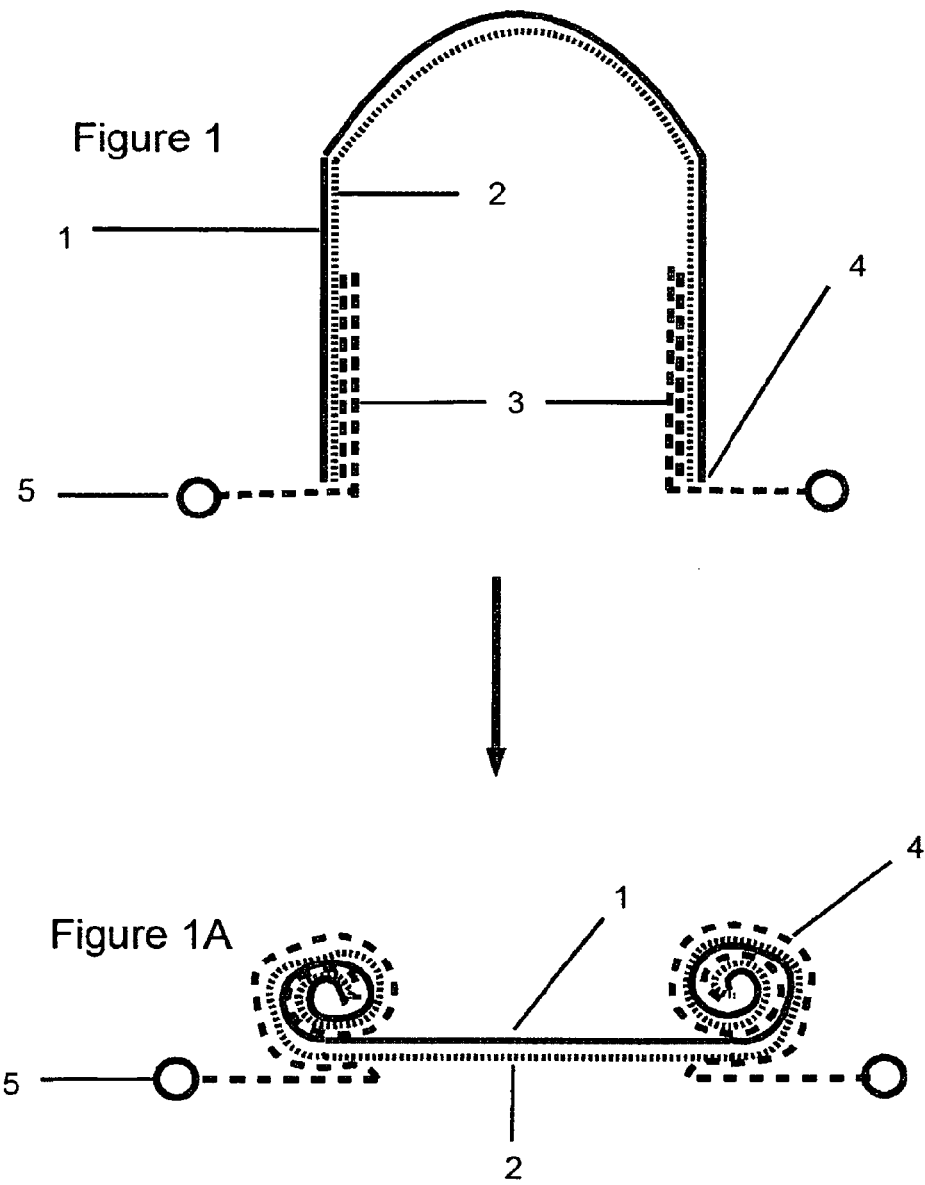
FIG. 1 is prior to deployment, FIG. 1A after. In both FIGS. 1 and 1A, Item 1 is the substance of the condom, Item 2 is the inner adhesive coating, Item 3 is the non-adherent backing membrane, Item 4 is the rolled edge of the condom, Item 5 is the deployment ring. (Please note that the final unit is a sandwich of condom, adhesive and backing membrane. The substance of the Condom (Item 1) therefore parallels that of the non-adherent membrane lining it (Item 3). Condom is rolled from exposed edge towards distal end of condom. Adhesive at center of condom remains exposed. OF NOTE: The region identified by arrows 1 and 2 also constitutes the "central diaphragm surface" noted in the Independent Claim; as this region is bordered by a stiff rolled rim, this central diaphragm surface will be under some tension and will therefore be flat prior to deployment, as illustrated in the drawing; it will also be noted that in this region the adhesive (if any is present) remains exposed on the inner surface. (Condom may be provided with reservoir at tip.)

Sheet 2 (FIG. 2, longitudinal side view in cross section) demonstrates the position of the device relative to the target prior to deployment. Same legend as drawing 1. Additional Item 6 represents target (male sexual organ). OF NOTE: As in the prior Drawing 1, the region identified by arrows 1 and 2 also constitutes the "central diaphragm surface" noted in the Independent Claim; as this region is bordered by a stiff rolled rim, this central diaphragm surface will be under some tension and will therefore be flat prior to deployment, as illustrated in the drawing; it will also be noted that in this region the adhesive (if any is present) remains exposed on the inner surface. (Please note that in preparation of deployment the packaged assembly is positioned against the tip of the target.)

Figure 2:
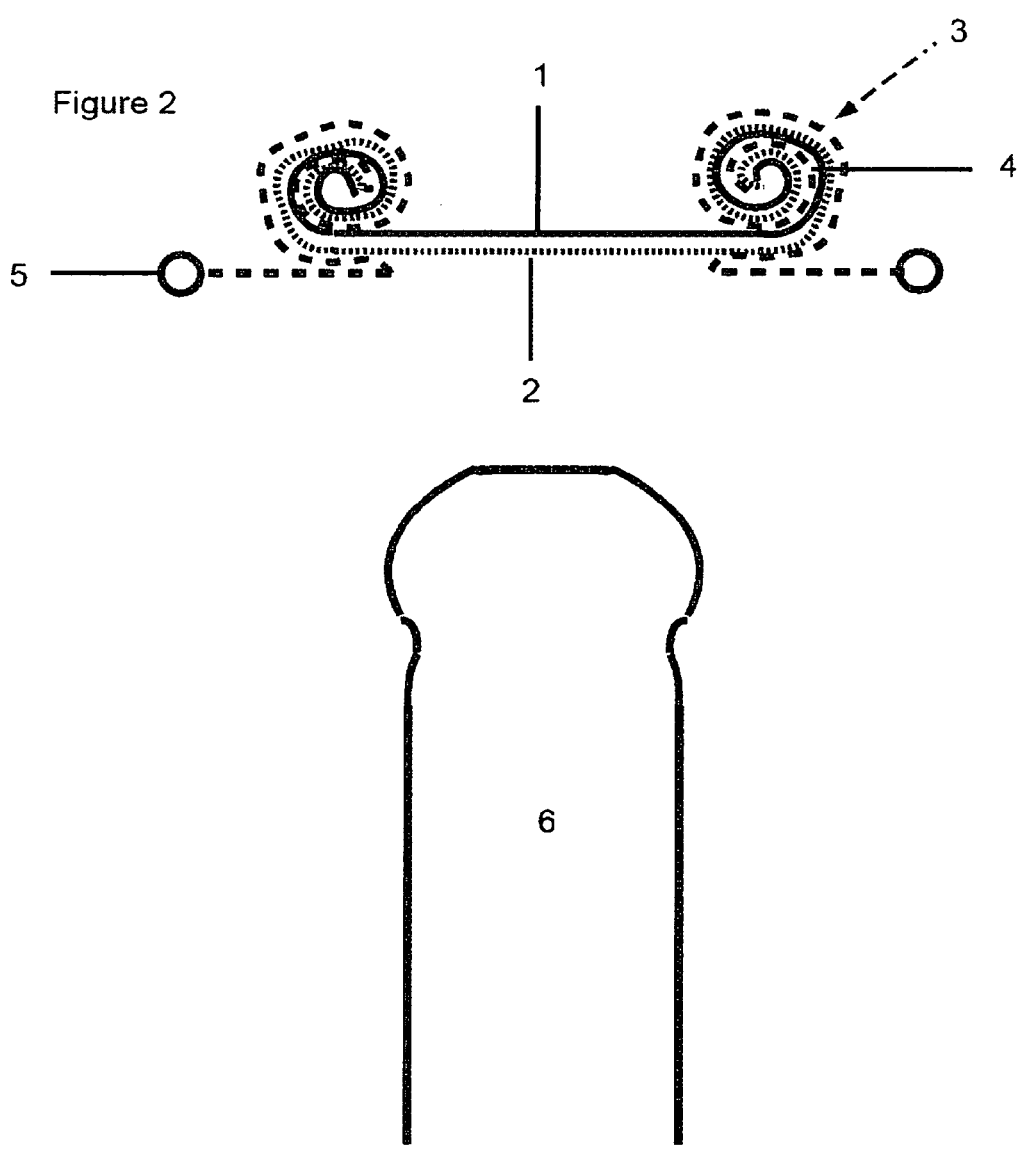

Sheet 3 (longitudinal top view in cross section) demonstrates the position of the device relative to the target prior to deployment from a different vantage point than FIG. 2. OF NOTE: As in the prior drawings, the region identified by arrows 1 and 2 also constitutes the "central diaphragm surface" noted in the Independent Claim; as this region is bordered by a stiff rolled rim, this central diaphragm surface will be under some tension and will therefore be flat prior to deployment, as illustrated in the drawing; it will also be noted that in this region the adhesive (if any is present) remains exposed on the inner surface. Same legend as FIG. 2 with identical comments.

Figure 4:
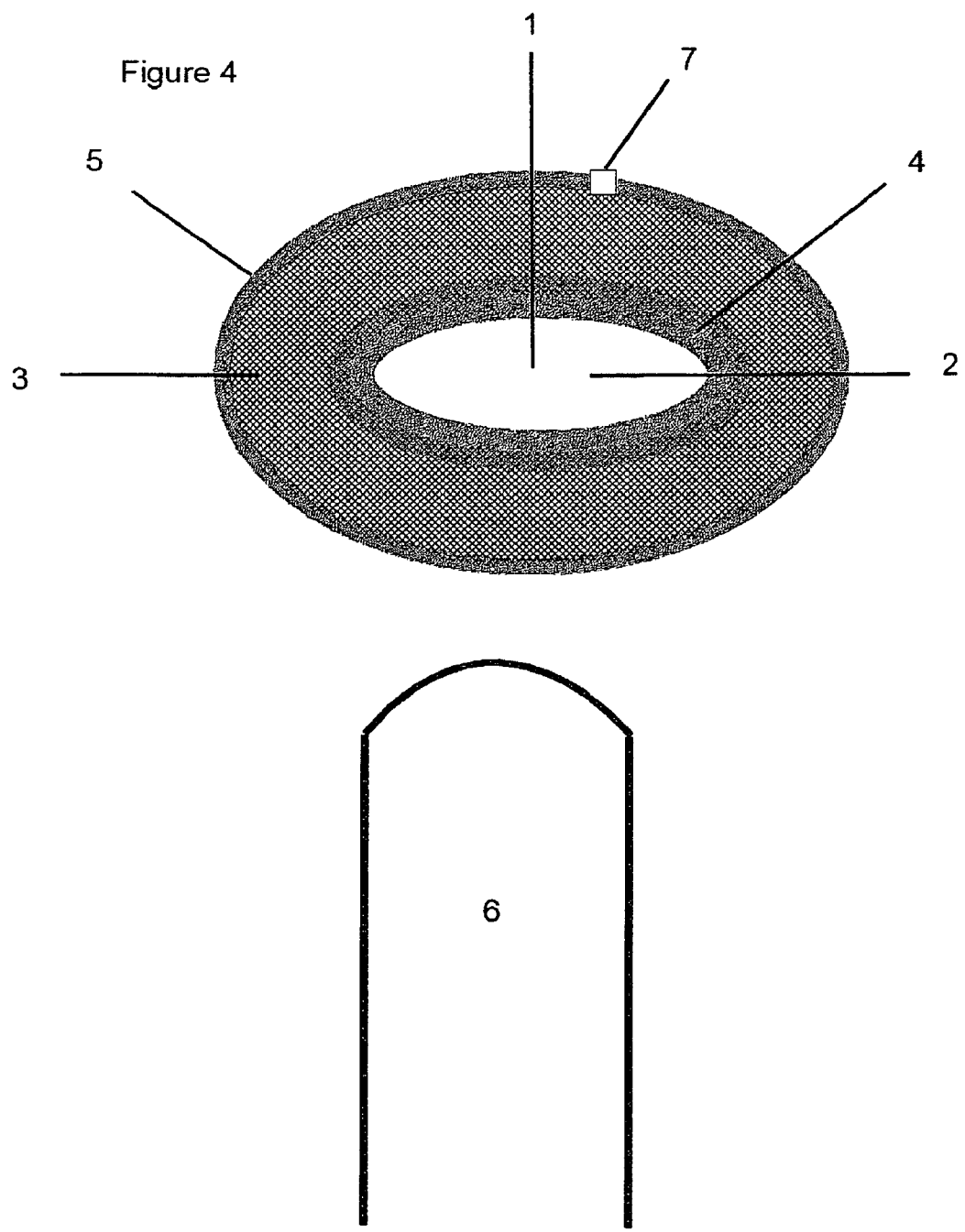

Sheet 4 (FIG. 4, oblique frontal view) demonstrates the position of the device relative to the target prior to deployment. Same legend and same comment as FIGS. 2 and 3. Additional Item 7 represents a split in the deployment ring, to permit easy removal after deployment. OF NOTE: As in the prior drawings, the region identified by arrow 1 also constitutes the "central diaphragm surface" noted in the Independent Claim; as this region is bordered by a stiff rolled rim, this central diaphragm surface will be under some tension and will therefore be flat prior to deployment, as illustrated in the drawing; it will also be noted that in this region the adhesive (if any is present) remains exposed on the inner surface (not shown in this view, since it is on the underside of the device).

Figure 5:
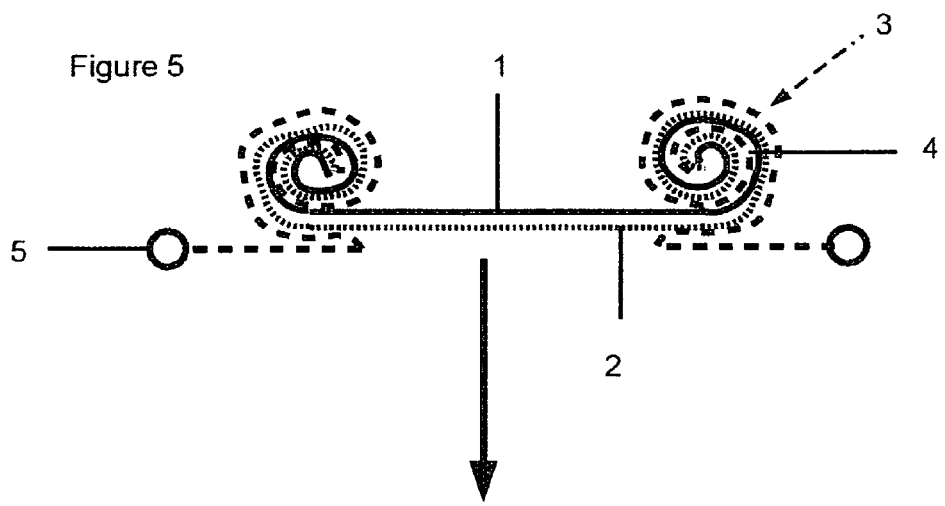
Figure 5A:
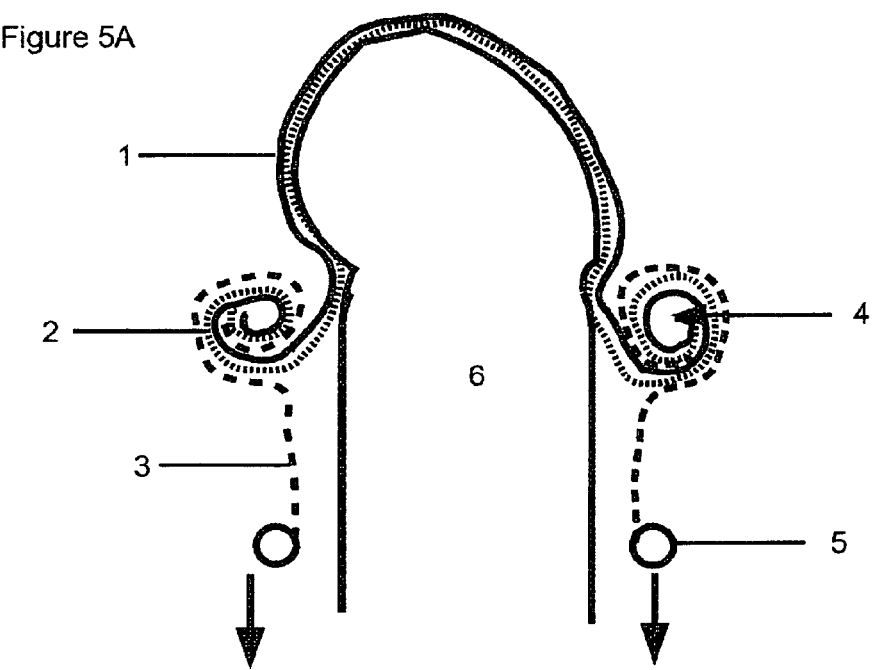

Sheet 5 (FIGS. 5 and 5A, longitudinal side view in cross section) clarifies the process of deployment onto the target. FIG. 5 illustrates the condom/backing membrane assembly just prior to deployment, whereas FIG. 5A illustrates the assembly partially deployed onto the target. Note that removal of the backing membrane from the base of the target has been initiated. Same legend as prior drawings. OF NOTE: As in the prior drawings, the region identified by arrows 1 and 2 also constitutes the "central diaphragm surface" noted in the Independent Claim; as this region is bordered by a stiff rolled rim, this central diaphragm surface will be under some tension and will therefore be flat prior to deployment, as illustrated in the drawing; it will also be noted that in this region the adhesive (if any is present) remains exposed on the inner surface. (Please note that the condom is rolled onto the target by pulling on the deployment ring. This action also initiates the removal of the non-adherent membrane from the base of the target.)

Figure 6:
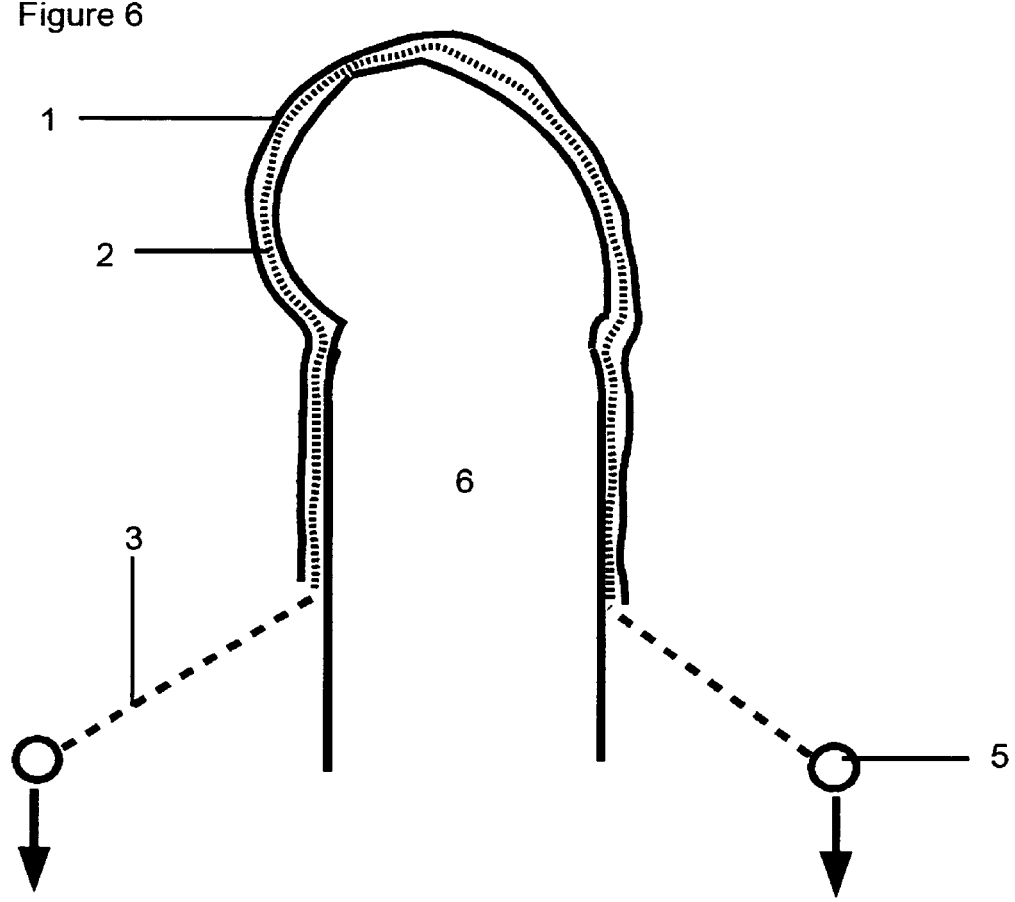

Sheet 6 (FIG. 6, longitudinal side view in cross section) illustrates a fully deployed device in the working configuration. OF NOTE: As in the prior drawings, the region identified by arrows 1 and 2 also constitutes the "central diaphragm surface" noted in the Independent Claim; as this region was bordered by a stiff rolled rim, it was thus flat prior to deployment; however, since this image shows a post-deployment view, the rim has been unrolled and this area is no longer flat, but rather conforms to the target geometry. Same legend as prior drawings. (Please note that the deployment ring is separated at the precut location and the backing membrane is pulled away from the target after full deployment.)

NOTE THAT THE CONDOM IS COATED ON ITS INNER SURFACE WITH AN ADHESIVE. IT IS INTENDED TO ADHERE TO TARGET. THE BACKING MEMBRANE IS NON-ADHESIVE AND IS ONLY PROVIDED FOR PACKAGING AND DEPLOYMENT. IF THE CONDOM LACKS AN ADHESIVE, THEN THE BACKING MEMBRANE MAY BE SLIGHTLY ADHESIVE TO FACILITATE DEPLOYMENT.

NOTE ALSO THAT RESERVOIR AT TIP IS NOT ILLUSTRATED, BUT IS ASSUMED.

DETAILED DESCRIPTION OF THE INVENTION

The condom is manufactured of a much thinner and preferably non-elastic, but distensible artificial membrane. Specifically, the membrane utilized should at least be plastic, meaning capable of deforming to adapt to the penis without retaining elastic forces to compress the penis once applied.

The membrane of manufacture should be permeable to gases and air (for instance, GoreTex™, generically known as polytetrafluoroethylene monopolymer). The membrane may also be partially permeable to liquids and particulates at least an order of magnitude smaller than the smallest viruses known.

It is preferred, but not prohibited, that condoms not be manufactured from latex. While the most prevalent condom material used today, latex condoms require very thick layers and have too many imperfections to work effectively. This is known, but proprietary information discussed in closely held public health documents.

A firm adhesive is to be applied to the inside of the condom. The adhesive fixes the condom to the skin of the penis. Appropriate adhesion will ensure that the condom is supported by the underlying skin and is much less likely to tear (in fact, even molecular layers of sufficient plasticity are impossible to tear unless the skin underneath tears). This means that the condom material can be many times thinner than the thinnest condoms currently in use. Further, compression is eliminated, thereby permitting normal erection. Compliance (i.e.: material conformability and utilization rates) is increased.

Of note, in its preferred embodiment this condom will be enhanced with antiseptic properties integrated to within the membrane. This may consist of bonded antibiotics, antivirals or other. Silver impregnate may work well.

Similar properties, as well as vasodilators, may also be integrated into the adhesive.

As alluded, a unique embodiment is envisioned to integrate a variety of special valvular mechanisms at the end of the condom to either permit re-use with the same partner, or to permit procreative activity while retaining barrier type protection. A separate and concurrent application is submitted for this improvement.

The invention claimed is:

1. An assembly comprising:
   a condom constructed of a flexible material and capable of providing a barrier to the passage of bodily fluids, microorganisms, and viruses;
   a backing membrane constructed of a flexible material in the shape of a hollow cylinder with proximal and distal open ends, wherein the proximal end flares out into a graspable thickened portion;
   the backing membrane is disposed along the inner surface of the condom;
   a package containing the condom and the backing membrane rolled along the length of the condom, wherein the proximal end of the backing membrane extends beyond the circumference of the condom, resulting in a ring with a graspable rim on the outside of the rolled condom; and
   during donning of the condom the ring is grasped by the user and pulled down over the glans penis, causing the condom to unroll over the glans penis.

2. The assembly of claim 1, wherein the condom is coated along at least a portion of the inside surface of the condom, which contacts the skin of the penis after deployment of the assembly, with an adhesive.

3. The assembly of claim 2, wherein the adhesive includes a spermicide to reduce the incidence of pregnancy.

4. The assembly of claim 2, wherein the adhesive includes a vasodilator to enhance erection.

5. The assembly of claim 2, wherein at least one of the condom and the coating on at least a portion of the inner surface of the condom that contacts the skin of the penis after deployment of the assembly is impregnated with at least one of a silver compound, an inert antiseptic, an antibiotic, an antiviral compound.

6. The assembly of claim 1, wherein the assembly further comprises sufficient fluorescence or chemoluminescence on an outer surface to permit localization and use of said condom in the dark.

7. The assembly of claim 6, wherein the fluorescence or the chemoluminescence is distributed in unequal fashion to permit differentiation of the inner surface of said condom that is coated with an adhesive from the outer surface of said condom that is not coated with an adhesive.

8. The assembly of claim 1, wherein said condom is turned inside out prior to application of said backing membrane.

9. The assembly of claim 1, wherein said assembly is rolled outwards over the cylinder defined by defined by the backing layer when packaged.

10. The assembly of claim 1, wherein said assembly is rolled inwards into the cylinder defined by the backing membrane when packaged.

11. The assembly of claim 1, wherein said graspable thickened portion is severable to facilitate easy removal of the backing membrane after deployment.

12. The assembly of claim 1, wherein said backing membrane can be easily broken to allow easy removal after deployment.

13. The assembly of claim 1, wherein said condom and said backing membrane adhere to each other along at least a portion of their contact area.

14. The assembly of claim 1, wherein graspable ring is a rigid or semi-rigid graspable ring to assist with deployment; and wherein said graspable ring is easily broken or provided with a discontinuity to facilitate ease of removal from the shaft of the penis after deployment of the assembly.

15. The assembly of claim 1, wherein the condom further comprises a storage reservoir to receive semen from the glans penis.

16. The assembly of claim 2, wherein the adhesive requires a specific solvent to permit removal of said condom from the skin of the penis for the reduction of transmission of sexually transmissible diseases.

17. The assembly of claim 1, wherein said condom is modified with a material or texture to enhance friction or achieve specific tuning characteristics to enhance sensation to the user.

\* \* \* \* \*